(12) United States Patent
Gildea et al.

(10) Patent No.: US 11,083,560 B2
(45) Date of Patent: Aug. 10, 2021

(54) METHODS OF TREATING AIRWAY STENOSIS

(71) Applicants: THE CLEVELAND CLINIC FOUNDATION, Cleveland, OH (US); New COS, Inc., Cleveland, OH (US)

(72) Inventors: Thomas Gildea, Cleveland, OH (US); Keith Grafmeyer, Cleveland, OH (US)

(73) Assignees: THE CLEVELAND CLINIC FOUNDATION, Cleveland, OH (US); NEW COS INC, Cleveland, OH (US)

(*) Notice: Subject to any disclaimer, the term of this patent is extended or adjusted under 35 U.S.C. 154(b) by 24 days.

(21) Appl. No.: 16/742,002

(22) Filed: Jan. 14, 2020

(65) Prior Publication Data
US 2020/0229914 A1    Jul. 23, 2020

Related U.S. Application Data

(60) Provisional application No. 62/793,452, filed on Jan. 17, 2019.

(51) Int. Cl.
*A61F 2/04* (2013.01)

(52) U.S. Cl.
CPC .......... *A61F 2/04* (2013.01); *A61F 2002/046* (2013.01); *A61F 2240/002* (2013.01); *A61F 2250/0059* (2013.01)

(58) Field of Classification Search
CPC .................. A61F 2/04; A61F 2002/826; A61F 2002/046; A61F 2002/043; A61F 2240/002; A61F 2002/065; G01N 2800/323; A61M 29/00
See application file for complete search history.

(56) References Cited

U.S. PATENT DOCUMENTS

| 9,629,705 B2 | 4/2017 | Douthitt et al. |
| 2017/0057169 A1 | 3/2017 | Grbic et al. |

OTHER PUBLICATIONS

Press Release from Toulouse University Hospital (CHU de Toulouse) Toulouse, Feb. 22, 2017 (Year: 2017).*
Freitag, Lutz, et al. "Towards individualized tracheobronchial stents: technical, practical and legal considerations." Respiration 94.5 (2017): 442-456.
Cheng, George Z., et al. "3D printing and personalized airway stents." Pulmonary Therapy 3.1 (2017): 59-66.
Dutau, Hervé, et al. "Biodegradable airway stents—bench to bedside: a comprehensive review." Respiration 90.6 (2015): 512-521.

* cited by examiner

*Primary Examiner* — Brian A Dukert
*Assistant Examiner* — Rebecca Lynee Zimmerman
(74) *Attorney, Agent, or Firm* — Tarolli, Sundheim, Covell & Tummino LLP

(57) ABSTRACT

Methods of treating airway stenosis are provided. Methods include gradually dilating the stenotic region of a patient's airway lumen with sequentially implanted customized airway stents. The airway stents are sequentially implanted until the diameter of the stenotic region of the patient's airway has substantially the same diameter as the diameter of an adjacent healthy region of the patient's airway lumen.

5 Claims, 2 Drawing Sheets

METHODS OF TREATING AIRWAY STENOSIS

RELATED APPLICATION

This application claims priority from U.S. Provisional Application No. 62/793,452, filed 17 Jan. 2019, the subject matter of which is incorporated herein by reference in its entirety.

GOVERNMENT FUNDING STATEMENT

This invention was made with government support under HL119810 awarded by National Institutes of Health. The government has certain rights in the invention.

TECHNICAL FIELD

The present disclosure is directed to methods of treating airway stenosis by dilating the stenotic region of a patient's airway with sequentially implanted customized airway stents.

BACKGROUND

Airway stenosis, or central airway obstruction, is a congenital or acquired narrowing of the airway. Airway stenosis can be caused, for example, by malignant and benign tumors, congenital abnormalities, airway injury or trauma, endotracheal intubation, tracheostomy, chronic inflammatory disease, autoimmune diseases, and infections. Many cases of tracheal stenosis develop as a result of prolonged intubation or from a prior tracheostomy and worldwide airway stenosis is commonly related to tuberculosis infections. Airway stenosis is named according to the location of the narrowing along the airway from the larynx (laryngotracheal stenosis) to the trachea (tracheal stenosis) and bronchi (bronchial stenosis). Treatment options for airway stenosis range from endoscopic dilatational techniques to open surgical procedures. Open and endoscopic surgical procedures involve either increasing the diameter of the stenosed segment with a graft or stent (expansion surgery) or removal of the stenotic area (resection surgery). Endoscopic techniques may involve the use of instruments to incise and dilate and stent the stenosis.

Currently, a common method of treating stenosis is to implant discretely-sized stents that inherently fit complex anatomy poorly. This poor fit leads to complications such as, but not limited to, granulation tissue formation, tissue necrosis, inflammation, and migration of the stent. In turn, these complications can result in restenosis or exacerbated airway problems. Replacements of these discretely-sized stents can be as frequent as every thirty days and require rigid bronchoscopy under general anesthesia. The choice of specific procedure or stent is based on general principles of minimal interventions as often treatments can induce more injury that the primary insult specifically in benign inflammatory conditions.

SUMMARY

According to an embodiment, a method of treating airway stenosis in a patient can comprise diagnosing a patient with stenosis of an airway lumen, where the airway lumen has a stenotic region and a healthy region. A method can comprise obtaining an internal image of the patient's chest showing the stenotic region and the healthy region of the airway lumen. The method can then include obtaining a patient-specific airway stent having a portion (referred to herein as the "active portion") dimensioned and sized for placement at the stenotic region. The active portion can have a diameter greater than the diameter of the stenotic region, the diameter of the stenotic region being determined from the internal image of the patient's chest. The method can further include implanting the patient-specific airway stent in the patient's airway lumen with the active portion positioned inside the stenotic region. The method can then include leaving the patient-specific airway stent in the patient's airway lumen until the diameter of the stenotic region increases to match the diameter of the stent. The patient-specific airway stent can then be removed from the patient's airway lumen. After that, the method can comprise obtaining another internal image of the patient's chest and obtaining another patient-specific airway stent having another active portion dimensioned and sized for placement at the stenotic region. The another active portion can have a diameter greater than the increased diameter of the stenotic region. The increased diameter of the stenotic region can be determined from the another internal image of the patient's chest. The method can further comprise implanting the another patient-specific airway stent in the patient's airway lumen with the another active portion positioned inside the stenotic region. The steps can be repeated until the stenotic region of the patient's airway lumen has a substantially equal diameter to the healthy region of the patient's airway lumen.

DETAILED DESCRIPTION

As used herein with respect to a described element, the terms "a," "an," and "the" include at least one or more of the described element unless otherwise indicated. Further, the term "or" refers to "and/or" unless otherwise indicated. As used herein, a "patient" is preferably a human being.

Figure 1:
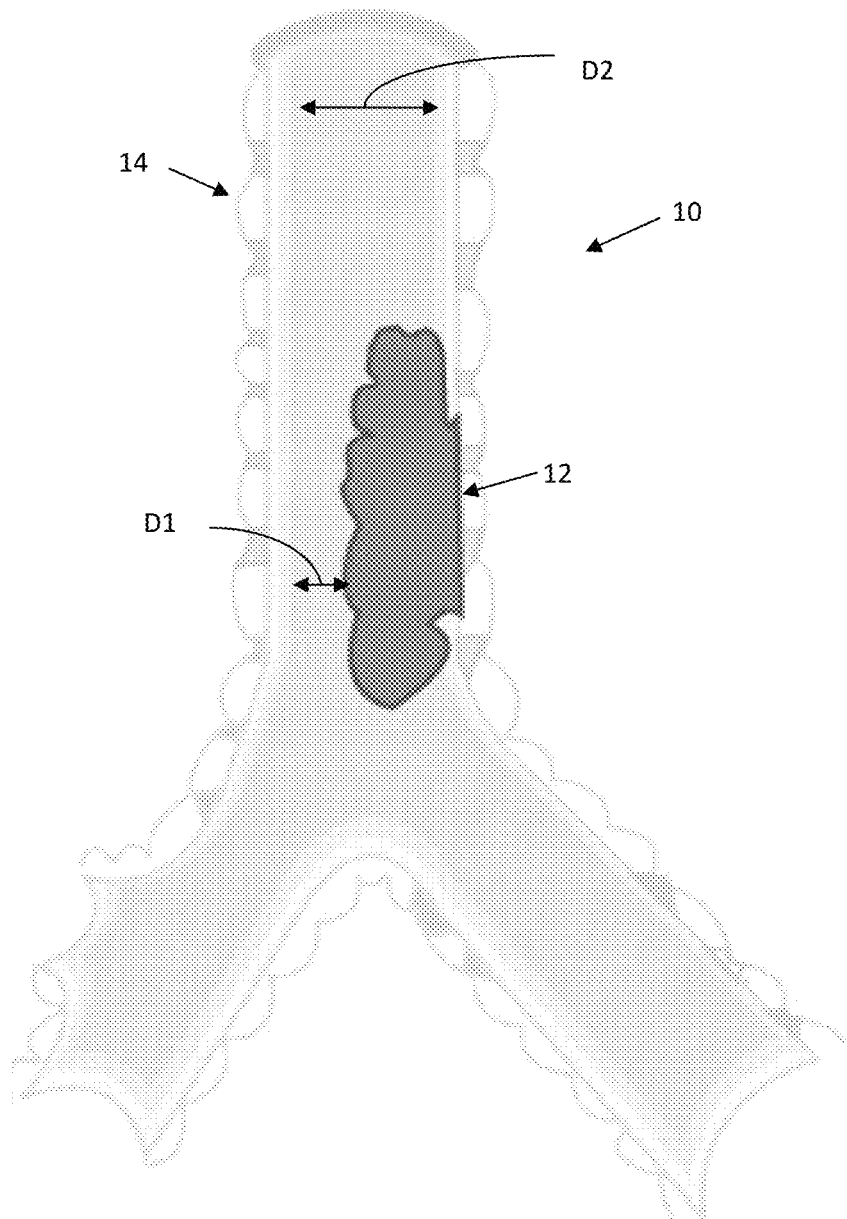
FIG. 1 is a schematic illustration of endoluminal central airway stenosis at the level of the distal trachea.

Methods of treating airway stenosis in a patient suffering therefrom are provided. Disclosed methods can involve gradually dilating or re-shaping a stenotic region of an airway lumen in a patient by implanting a series of customized patient-specific airway stents based on small airway changes over time. Without wishing to be bound by theory, it is believed that airway remodeling can occur as airway inflammation resolves with proper airway support as a result of appropriate stent sizing. A well-fitted stent can reduce pressure points in the airway that lead to complications that can exacerbate a condition. Minimally traumatic dilation of the airway leads to airway tissue acceptance. For purposes of illustration and a better understanding of the context of the present disclosure, FIG. 1 illustrates endoluminal central airway stenosis at the level of the distal trachea 10. Distal trachea 10 comprises a healthy tracheal region 14 having a diameter D2 and an adjacent stenotic region 12 having a diameter D1. Disclosed methods can result in stenotic region 14 of the patient's trachea 10 ultimately having a substantially equal diameter to healthy region 12 of the patient's trachea 10 such that at least one symptom of the patient's airway stenosis is relieved. In general, a clinically significant stenosis is one where the airway lumen is greater than 50% occluded/stenotic and a successful stent improves the airway lumen more than 50% in relative proportion or that approach's a native normal healthy airway lumen. Although FIG. 1 illustrates the distal trachea, methods can be used for other components of the patient's airway that have a stenotic region such as other areas of the trachea, larynx, bronchi, or combinations thereof.

Figure 2:
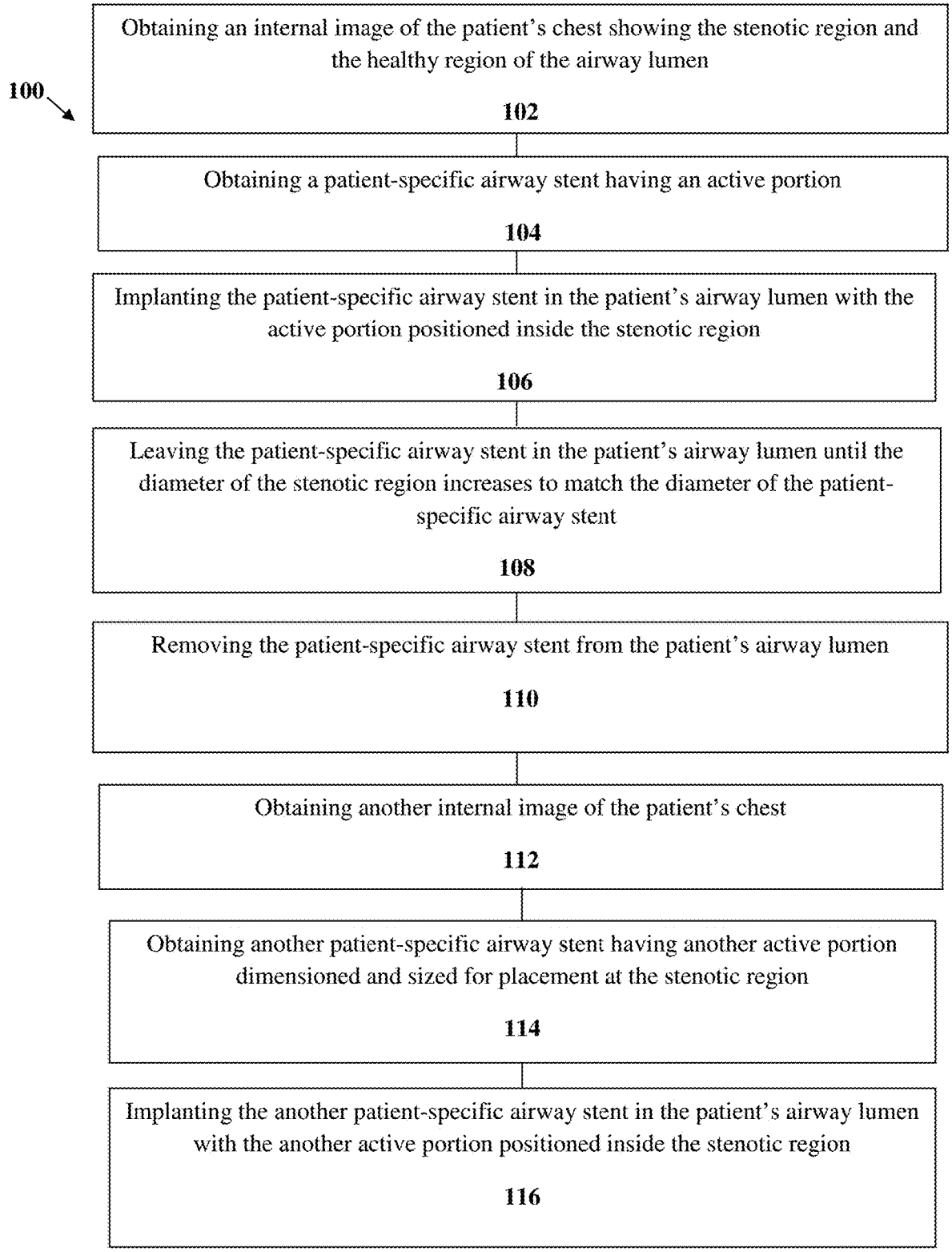
FIG. 2 is a flow chart depicting steps of a method of treating airway stenosis according to an embodiment of the present disclosure.

According to an embodiment, a method of treating airway stenosis in a patient can comprise diagnosing a patient with stenosis of an airway lumen, where the airway lumen has a stenotic region and a healthy region. The stenosis can be caused by, for example, benign or malignant disease although disclosed methods may be more beneficial in patients with benign disease since such patients have longer life expectancy. Referring to FIG. 2, a method (100) can comprise obtaining an internal image of the patient's chest showing the stenotic region and the healthy region of the airway lumen (102). Such internal image can be, for example, a computer tomography (CT) image, a magnetic resonance imaging (MRI) image, an ultrasound image, or combinations thereof. Method (100) can then include obtaining a patient-specific airway stent comprising a tubular body, for example, having an active portion dimensioned and sized for placement at the stenotic region (104). The active portion can have a diameter greater than the diameter of the stenotic region, the diameter of the stenotic region being determined from the internal image of the patient's chest. In each prescription of the patient-specific airway stent, the diameter of the active portion of the patient-specific airway stent can be increased to adjust for the change related to the underlying disease. Method 100 can further include implanting the patient-specific airway stent in the patient's airway lumen with the active portion positioned inside the stenotic region (106). Method 100 can then include leaving the patient-specific airway stent in the patient's airway lumen until the diameter of the stenotic region increases to match the diameter of the patient-specific airway stent (108). The patient-specific airway stent can be left in the patient's airway lumen for a clinically relevant period of time that can be a variable amount of time based on the patient's underlying pathology. In a non-limiting example, the stent is left in the patient's airway lumen for up to one year. Removal prior to this would be due to, for example, adverse events experienced by the patient or worsening symptoms. The patient-specific airway stent can then be removed from the patient's airway lumen (110). After that, method 100 can comprise obtaining another internal image of the patient's chest (112) and obtaining another patient-specific airway stent comprising a tubular body, for example, having another active portion dimensioned and sized for placement at the stenotic region (114). The another active portion can have a diameter greater than the increased diameter of the stenotic region. The increased diameter of the stenotic region can be determined from the another internal image of the patient's chest. Method 100 can further comprise implanting the another patient-specific airway stent in the patient's airway lumen with the another active portion positioned inside the stenotic region (116). Steps 102-116 can be repeated until the stenotic region of the patient's airway lumen has a substantially equal diameter to the healthy region of the patient's airway lumen.

Non-limiting examples of conditions associated with airway stenosis that can be treated according to disclosed methods are benign airway tumors, bronchial stenosis, carinal tumors and stenosis, malignant airway tumors, tracheobronchial injuries, tracheobroncial malacia, tracheomalacia, and combinations thereof. The customized patient-specific airway stents can be sized and dimensioned for implantation in at least a portion of the patient's airway such as the larynx, the trachea, a bronchus, or combinations thereof. Also the diameter and angles can be varied throughout the patient-specific stent to reduce complications associated with poor fit that can lead to restenosis. These complications include, but are not limited to, granulation tissue formation, tissue necrosis, inflammation, and migration. We also believe that the stent should be tubular in structure to deliver uniform resistance in the stenotic region. The stents can be tubular in structure to deliver uniform resistance in the stenotic region.

Each of the disclosed aspects and embodiments of the present disclosure may be considered individually or in combination with other aspects, embodiments, and variations of the disclosure. Unless otherwise specified, none of the steps of the methods of the present disclosure are confined to any particular order of performance.

What is claimed is:

1. A method of treating airway stenosis in a patient suffering therefrom comprising:
   (a) obtaining an internal image of a chest of a patient having an airway lumen with a stenotic region and a healthy region;
   (b) obtaining a patient-specific airway stent comprising a tubular body having a portion dimensioned and sized for placement at the stenotic region, the portion having a diameter greater than the diameter of the stenotic region, the diameter of the stenotic region determined from the internal image of the patient's chest;
   (c) implanting the patient-specific airway stent in the patient's airway lumen with the portion positioned inside the stenotic region;
   (d) leaving the patient-specific airway stent in the patient's airway lumen until the diameter of the stenotic region increases to match the diameter of the stent;
   (e) removing the patient-specific airway stent from the patient's airway lumen;
   (f) obtaining another internal image of the patient's chest;
   (g) obtaining another patient-specific airway stent comprising a tubular body having another portion dimensioned and sized for placement at the stenotic region, the another portion having a diameter greater than the increased diameter of the stenotic region, the increased diameter of the stenotic region determined from the another internal image of the patient's chest;
   (h) implanting the another patient-specific airway stent in the patient's airway lumen with the another portion positioned inside the stenotic region; and
   (i) repeating steps (a) through (h) until the stenotic region of the patient's airway lumen has a substantially equal diameter to the healthy region of the patient's airway lumen.

2. A method of treating airway stenosis in a patient suffering therefrom comprising:
   (a) obtaining an internal image of a chest of a patient having an airway lumen with a stenotic region and a healthy region;
   (b) obtaining a patient-specific airway stent comprising a tubular body having a portion dimensioned and sized for placement at the stenotic region, the portion having a diameter greater than the diameter of the stenotic region, the diameter of the stenotic region determined from the internal image of the patient's chest;
   (c) implanting the patient-specific airway stent in the patient's airway lumen with the portion positioned inside the stenotic region;

(d) leaving the patient-specific airway stent in the patient's airway lumen for a clinically relevant period of time;
(e) removing the patient-specific airway stent from the patient's airway lumen;
(f) obtaining another internal image of the patient's chest;
(g) obtaining another patient-specific airway stent comprising a tubular body having another portion dimensioned and sized for placement at the stenotic region, the another portion having a diameter greater than the diameter of the stenotic region, the increased diameter of the stenotic region determined from the another internal image of the patient's chest;
(h) implanting the another patient-specific airway stent in the patient's airway lumen with the another portion positioned inside the stenotic region; and
(i) repeating steps (a) through (h) until the stenotic region of the patient's airway lumen has a substantially equal diameter to the healthy region of the patient's airway lumen.

3. The method of claim 1 or 2, wherein obtaining an internal image and/or obtaining another internal image comprises obtaining a computer tomography (CT) image, a magnetic resonance imaging (MRI) image, or an ultrasound image, or combinations thereof.

4. The method of claim 2, wherein the clinically relevant period of time is up to one year.

5. The method of claim 2, wherein obtaining an internal image and/or obtaining another internal image comprises obtaining a computer tomography (CT) image, a magnetic resonance imaging (MRI) image, or an ultrasound image, or combinations thereof.

\* \* \* \* \*